(12) United States Patent
Neumann

(10) Patent No.: US 11,961,605 B2
(45) Date of Patent: Apr. 16, 2024

(54) METHODS AND SYSTEMS FOR INFORMING SELF-TREATMENT REMEDY SELECTION

(71) Applicant: KPN Innovations, LLC, Lakewood, CO (US)

(72) Inventor: Kenneth Neumann, Lakewood, CO (US)

(73) Assignee: KPN Innovations, LLC, Lakewood, CO (US)

(*) Notice: Subject to any disclaimer, the term of this patent is extended or adjusted under 35 U.S.C. 154(b) by 0 days.

(21) Appl. No.: 16/699,420

(22) Filed: Nov. 29, 2019

(65) Prior Publication Data

US 2021/0166802 A1    Jun. 3, 2021

(51) Int. Cl.
| | | |
|---|---|---|
| *G16H 20/60* | (2018.01) | |
| *G06N 20/00* | (2019.01) | |
| *G16H 10/60* | (2018.01) | |
| *G16H 50/50* | (2018.01) | |
| *G16H 70/60* | (2018.01) | |

(52) U.S. Cl.
CPC ............ *G16H 20/60* (2018.01); *G06N 20/00* (2019.01); *G16H 10/60* (2018.01); *G16H 50/50* (2018.01); *G16H 70/60* (2018.01)

(58) Field of Classification Search
CPC ........ G16H 50/20; G16H 10/60; G16H 40/20; G16H 40/63; G16H 80/00; G16H 40/67; G16H 10/20; G16H 50/70; G16H 20/60; G16H 70/60; G16H 50/50; G16H 20/10; G06F 19/30; G06F 19/32; G06F 19/34; G06F 19/36; G06F 3/0484; G06Q 50/22; G06Q 50/24; A61B 5/00; A61B 5/145; A61B 5/168; A61B 5/1118; A61B 5/4815; A61B 5/165; H04L 29/08; H04L 12/24; G06N 20/00; Y02A 90/10
See application file for complete search history.

(56) References Cited

U.S. PATENT DOCUMENTS

| | | |
|---|---|---|
| 8,884,752 B2 | 11/2014 | Tai et al. |
| 10,262,107 B1 | 4/2019 | Tran et al. |
| 10,362,987 B2 | 7/2019 | Hong |

(Continued)

FOREIGN PATENT DOCUMENTS

CN       109087691       12/2018

OTHER PUBLICATIONS

Collins, Artificial Intelligence Helps Stanford Computer Scientists Predict the Side Effects of Millions of Drug Combinations, (web post), Jul. 10, 2018, Stanford News.

*Primary Examiner* — Peter H Choi
*Assistant Examiner* — Shyam M Goswami
(74) *Attorney, Agent, or Firm* — Caldwell Intellectual Property Law

(57) ABSTRACT

A system for informing self-treatment remedy selection. The system includes a computing device configured to identify a self-treatment remedy associated with a user. The computing device classifies using a remedy classify an identified self-treatment remedy as an input and outputs a self-treatment model. The computing device retrieves a biological extraction associated with a user and calculates a self-treatment model using a machine-learning model. The computing device generates a remedy label and determines using the remedy label if an identified self-treatment remedy is safe for user consumption.

18 Claims, 6 Drawing Sheets

(56) References Cited

U.S. PATENT DOCUMENTS

| | | | |
|---|---|---|---|
| 2004/0171056 A1* | 9/2004 | Stanton, Jr. | C12Q 1/6883 435/6.16 |
| 2010/0042430 A1* | 2/2010 | Bartfeld | G06Q 10/10 705/2 |
| 2013/0268296 A1* | 10/2013 | Byer | G06Q 50/22 705/3 |
| 2014/0058755 A1* | 2/2014 | Macoviak | G16H 10/60 705/3 |
| 2016/0048655 A1* | 2/2016 | Maitra | G16H 20/10 705/3 |
| 2017/0165194 A1* | 6/2017 | Meng | A61Q 19/00 |
| 2018/0181719 A1* | 6/2018 | Balian | G16H 40/20 |
| 2018/0365385 A1 | 12/2018 | Cooney et al. | |
| 2019/0056414 A1 | 2/2019 | Millet, Jr. et al. | |
| 2019/0214121 A1 | 7/2019 | O'Keeffe et al. | |
| 2019/0272725 A1 | 9/2019 | Viklund et al. | |
| 2019/0304604 A1 | 10/2019 | Kupersmith et al. | |
| 2019/0311807 A1 | 10/2019 | Kannan et al. | |

\* cited by examiner

METHODS AND SYSTEMS FOR INFORMING SELF-TREATMENT REMEDY SELECTION

FIELD OF THE INVENTION

The present invention generally relates to the field of artificial intelligence. In particular, the present invention is directed to methods and systems for informing self-treatment remedy selection.

BACKGROUND

Appropriate selection of self-treatment remedies can be challenging, particularly to those without any knowledge or experience in selecting self-treatment remedies that will address a symptom but also be compatible with a user's body mechanics. Knowing which self-treatment remedies will be or will not be compatible with one's body is extremely difficult to predict with accuracy.

SUMMARY OF THE DISCLOSURE

In an aspect, a system for informing self-treatment remedy selection the system comprising a computing device the computing device designed and configured to identify a self-treatment remedy associated with a user. The system further configured to classify using a remedy classifier, the identified self-treatment remedy as an input and outputs a self-treatment model. The system further configured to retrieve a first biological extraction associated with the user. The system further configured to calculate the self-treatment model using a first machine-learning algorithm wherein the self-treatment model takes a user biological extraction as an input and outputs a remedy label. The system further configured to generate a remedy label using the first biological extraction and the self-treatment model. The system further configured to determine using the remedy label if the identified self-treatment remedy is safe for user consumption.

In an aspect, a method of informing self-treatment remedy selection. The method includes identifying by a computing device a self-treatment remedy associated with a user. The method includes classifying by the computing device using a remedy classifier, the identified self-treatment remedy as an input and outputs a self-treatment model. The method includes retrieving by the computing device a first biological extraction associated with the user. The method includes calculating by the computing device the self-treatment model using a first machine-learning algorithm wherein the self-treatment model takes a user biological extraction as an input and outputs a remedy label. The method includes generating by the computing device a remedy label using the first biological extraction and the self-treatment model. The method includes determining by the computing device using the remedy label if the identified self-treatment remedy is safe for user consumption.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for informing self-treatment remedy selection. In an embodiment, a system that includes a computing device identifies a self-treatment remedy associated with a user. A self-treatment remedy may be identified by receiving a user biological extraction and generating using a treatment model a machine-learning algorithm that relates biological extractions to self-treatment remedies. A self-treatment remedy may be identified by receiving a user symptom and generating using a symptomatic model a machine-learning algorithm that relates symptoms to self-treatment remedies. A computing device classifies using a remedy classifier an identified self-treatment remedy as an input and outputs a self-treatment model. A computing device retrieves a biological extraction associated with a user and calculates a self-treatment model using a machine-learning algorithm that utilizes the biological extraction associated with the user as an input and outputs a remedy label. A computing device generates a remedy label and determines using the remedy label if an identified self-treatment remedy is safe for user consumption.

Figure 1:
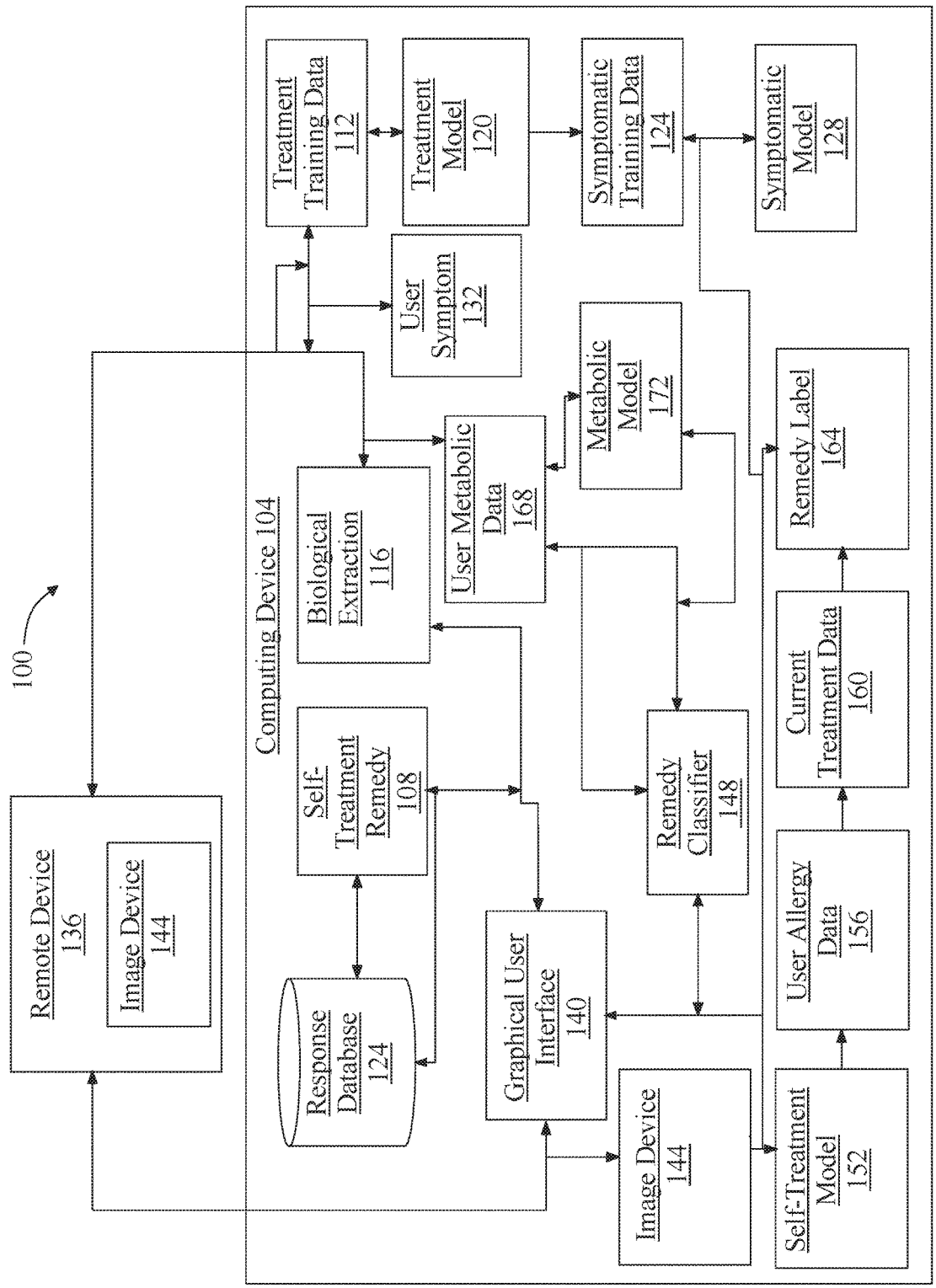
FIG. 1 is a block diagram illustrating an exemplary embodiment of a system for informing self-treatment remedy selection.

Referring now to FIG. 1, an exemplary embodiment of a system 100 for informing self-treatment remedy selection is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is designed and configured to identify a self-treatment remedy associated with a user. A "self-treatment remedy," as used in this disclosure, is any over the counter medication sold to a user without a prescription from a healthcare professional. A self-treatment remedy 108 may include any medication considered safe and effective for use by the general public without seeking treatment from a healthcare professional such as a medical doctor, physician assistant, nurse practitioner, podiatrist, dentist and the like. A self-treatment remedy 108 may include one or more medications sold on shelves in pharmacies, grocery stores, gas stores and the like. A self-treatment remedy 108 may include one or more restricted over the counter substances. A restricted over the counter substance may include one or more self-treatment remedies that may be stored behind a counter and may be sold only in stores or pharmacies registered within their state. A restricted over the counter substance may be unavailable in convenience and grocery stores that may sell other non-restricted self-treatment remedies. A restricted over the counter substance may include products containing active ingredients such as pseudoephedrine or may include one or more forms of emergency contraception. A restricted over the counter substance may be subject to record-keeping rules and quantity and/or age restrictions. A restricted over the counter substance may only be sold and dispensed by a pharmacy and may require consultation with a licensed pharmacist before sale. A self-treatment remedy 108 may be intended to treatment a variety of symptoms due to illnesses that an individual can self-treat such as pain, cough, cold, diarrhea, heartburn, constipation, skin rash, nausea, sunburn, acne and the like. A self-treatment remedy 108 may include for example sunscreens, anti-microbial and anti-fungal products, external and internal analgesics such as lidocaine, aspirin, psoriasis and eczema topical treatments, anti-dandruff shampoos containing coal tar, pain relievers such as ibuprofen and acetaminophen, and naproxen sodium, cough and cold medication such as guaifenesin, phenylephrine, pseudoephedrine, and dextromethorphan, antihistamines such as brompheniramine, cetirizine, chlorpheniramine, fexofenadine, diphenhydramine, and loratadine. A self-treatment remedy 108 may include an act or instance of medicating oneself or treating one's own disease without medical supervision or intervention. For instance and without limitation, a user who experiences a headache may select a self-treatment remedy 108 such as acetaminophen or ibuprofen. In yet another non-limiting example, a user who experiences a cold may select a self-treatment remedy 108 such as guaifenesin. In yet another non-limiting example, a user who experiences a sunburn may select a self-treatment remedy 108 such as aloe vera gel.

With continued reference to FIG. 1, computing device 104 may identify a self-treatment remedy 108 associated with a user by receiving treatment training data 112. Training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithm and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithm, and/or automated association of data in the data entry with descriptors or into a given format. The ability to categorize data entries automatedly may enable the same training data to be made applicable for two or more distinct machine-learning algorithm as described in further detail below. Training data used by processor 104 may correlate any input data as described in this disclosure to any output data as described in this disclosure.

With continued reference to FIG. 1, "treatment training data 112" as used in this disclosure, includes training data that contains a plurality of biological extraction 116 and a plurality of correlated self-treatment remedies. A "biological extraction 116" as used in this disclosure includes at least an element of user biological data. As used in this disclosure, "biological data" is any data indicative of a person's biological state; biological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, biological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, biological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Biological state data may include, without limitation, immune function data such as Interleukine-6 (IL-6), TNF-alpha, systemic inflammatory cytokines, and the like.

Continuing to refer to FIG. 1, biological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Biological state data may include measures of glucose metabolism such as fasting glucose levels and/or hemoglobin A1-C (HbA1c) levels. Biological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Biological state data may include measures of estimated glomerular filtration rate (eGFR). Biological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Biological state data may include antinuclear antibody levels. Biological state data may include aluminum levels. Biological state data may include arsenic levels. Biological state data may include levels of fibrinogen, plasma cystatin C, and/or brain natriuretic peptide.

Continuing to refer to FIG. 1, biological state data may include measures of lung function such as forced expiratory volume, one second (FEV-1) which measures how much air can be exhaled in one second following a deep inhalation, forced vital capacity (FVC), which measures the volume of air that may be contained in the lungs. Biological state data may include a measurement blood pressure, including without limitation systolic and diastolic blood pressure. Biological state data may include a measure of waist circumference. Biological state data may include body mass index (BMI). Biological state data may include one or more measures of bone mass and/or density such as dual-energy x-ray absorptiometry. Biological state data may include one or more measures of muscle mass. Biological state data may include one or more measures of physical capability such as without limitation measures of grip strength, evaluations of standing balance, evaluations of gait speed, pegboard tests, timed up and go tests, and/or chair rising tests.

Still viewing FIG. 1, biological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Biological state data may include one or more evaluations of sensory ability, including measures of audition, vision, olfaction, gustation, vestibular function and pain.

Continuing to refer to FIG. 1, biological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module 136 as described in this disclosure.

Still referring to FIG. 1, biological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Biological state data may include proteomic data, which as used herein is data describing all proteins produced and/or modified by an organism, colony of organisms, or system of organisms, and/or a subset thereof. Biological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other biological state data of a person, as described in further detail below.

With continuing reference to FIG. 1, biological state data may include one or more user-entered descriptions of a person's biological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Biological state data may include any biological state data, as described above, describing any multicellular organism living in or on a person including any parasitic and/or symbiotic organisms living in or on the persons; non-limiting examples may include mites, nematodes, flatworms, or the like. Examples of biological state data described in this disclosure are presented for illustrative purposes only and are not meant to be exhaustive.

With continued reference to FIG. 1, biological data may include, without limitation any result of any medical test, biological assessment, cognitive assessment, psychological assessment, or the like. System 100 may receive at least a biological data from one or more other devices after performance; system 100 may alternatively or additionally perform one or more assessments and/or tests to obtain at least a biological data, and/or one or more portions thereof, on system 100. For instance, at least biological data may include or more entries by a user in a form or similar graphical user interface 140 152 116 object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a biological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, biological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a biological sample consistent with this disclosure.

With continued reference to FIG. 1, biological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or biological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and biological properties, behavior, and products of behavior. Behavioral phenotypes may include cognitive, personality, and behavior patterns. This may include effects on cellular and biological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, *firmicutes, Bacteroidetes*, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, Giardia lamblia EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica,* Giardia, *H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as *Methanobrevibacter smithies'* and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as *Ackerman's muciniphila, Anaerotruncus colihominis*, bacteriology, *Bacteroides vulgates', Bacteroides-Prevotella, Barnesiella* species, *Bifidobacterium longarm, Bifidobacterium* species, Butyrivbrio crossotus, *Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, *Firmicutes* to *Bacteroidetes* ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosatetraenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of biological state data that may be used consistently with descriptions of systems and methods as provided in this disclosure.

With continued reference to FIG. 1, biological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Biological data may be obtained from a physically extracted sample. A physical sample may include a signal from a sensor configured to detect biological data of a user and record biological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, computing device 104 generates using a machine-learning algorithm a treatment model 120 relating biological extraction 116 to self-treatment remedies. Continuing to refer to FIG. 1, machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine-learning algorithms that may be used to determine relation between inputs and outputs.

With continued reference to FIG. 1, supervised machine-learning processes may include classification algorithm defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine-learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithms may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

Continuing to refer to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 1, computing device 104 records a user biological extraction 116 and outputs self-treatment remedies as a function of generating a treatment model. "Treatment model 120" as used in this disclosure, includes a machine-learning model that inputs a user biological extraction 116 and outputs self-treatment remedies. Treatment model 120 may include performing a series of one or more calculations, algorithms, and/or equations. Treatment model 120 may be generated using one or more machine-learning algorithms including any of the machine-learning algorithms as described above. For instance and without limitation, treatment model 120 may receive an input that includes a user biological extraction 116 such as a toenail culture that reveals toenail fungus with an output that includes self-treatment remedies that include clotrimazole or terbinafine.

With continued reference to FIG. 1, computing device 104 may identify a self-treatment remedy 108 associated with a user by receiving symptomatic training data 124. "Symptomatic training data" as used in this disclosure, is training data that contains a plurality of symptoms and a plurality of correlated self-treatment remedies. Training data includes any of the training data as described above. A "symptom" as used in this disclosure, is any physical or mental complaint experienced by a person that may indicate a condition or disease. A symptom may be experienced briefly such as an acute symptoms that comes on suddenly, or may be of a more prolonged nature such as a symptom that is experienced chronically or remitting. A symptom may be experienced in a specific organ or location of the body such as a symptom that is contained within a user's foot. A symptom may be experienced systemically or throughout the entire body such as fever, malaise, anorexia, or weight loss. A symptom may include a non-specific symptom such as a symptom that does not indicate a specific disease process or involved an isolated body system such as fatigue. A symptom may include a positive symptom such as a symptom present in a disorder but not normally experienced by most individuals. For example a positive symptom may include a symptom experienced in a mental disorder such as hallucinations, delusions or bizarre behavior. A symptom may include a negative symptom such as a function normally found in a healthy person but is diminished or not present in an affected person. A negative symptom may include a symptom that has disappeared from a person's normal way of functioning. A negative symptom may include social withdrawal, apathy, inability to experience pleasure.

With continued reference to FIG. 1, computing device 104 is configured to generate using a machine-learning algorithm a symptomatic model 128 relating symptoms to self-treatment remedies. "Symptomatic model" as used in this disclosure, is a machine-learning model that relates an input containing symptoms to an output containing self-treatment remedies. Symptomatic model 128 may include performing a series of one or more calculations, algorithms, and/or equations. Symptomatic model 128 may be generated using one or more machine-learning algorithms including any of the machine-learning algorithms as described above.

With continued reference to FIG. 1, computing device 104 is configured to receive a user symptom 132. A "user symptom 132" as used in this disclosure, includes any physical or mental complaint experienced by a user that may indicate a condition or disease that a user seeks to self-treat or treat without the assistance or guidance of medical treatment. A user symptom 132 may include a description of one or more symptoms that a user may be currently experiencing or may have experienced in the past. For instance and without limitation, a user symptom 132 may include a description of symptoms the user is currently experiencing such as a runny nose, sneezing, wet productive cough and body chills. In yet another non-limiting example, a user symptom 132 may include a description of symptoms the user experiences sporadically such as itchiness on user's forearms and forehead upon waking.

With continued reference to FIG. 1, computing device 104 may receive a user symptom 132 from a remote device 136 operated by a user. Remote device 136 may include without limitation, a display in communication with computing device 104, where a display may include any display as described herein. Remote device 136 may include an additional computing device, such as a mobile device, laptop, desktop, computer and the like. Remote device 136 may transmit and/or receive one or more inputs from computing device 104 utilizing any network methodology as described herein. Remote device 136 may be operated by a user which may include any human subject. Remote device 136 may be operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like. For example, a user may describe to user's functional medicine doctor at an appointment a series of one or more symptoms the user has been experiencing such as symptoms of a cold that include coughing, sore throat, runny nose, sneezing, headache and fever. In such an instance, an informed advisor may transmit from remote device 136 user's symptoms because informed advisor may be unable to prescribe any prescriptions or drugs that can resolve user's symptoms as only self-treatment remedies may be available to treat user's symptoms. User symptom 132 may be transmitted from a remote device 136 to computing device 104 utilizing any network methodology as described herein.

With continued reference to FIG. 1, computing device 104 may include a graphical user interface 140. Graphical user interface 140 may include without limitation a form or other graphical element having data entry fields, where a user may select one or more fields to enter one or more user symptoms 132. Graphical user interface 140 may provide a drop-down menu and display symptoms where a user may select one or more symptoms user may be experiencing. Symptoms may be displayed according to one or more classification systems such as symptoms experienced by location on body. For instance and without limitation, graphical user interface 140 may list symptoms located to abdomen that may include right upper quadrant pain, left upper quadrant pain, right lower quadrant pain, left lower quadrant pain, acute stabbing pain, dull chronic pain, pain after eating, pain upon waking, nighttime pain, pain after lying down, and the like. In such an instance, a user may select one or more symptoms that pertain to the user. Graphical user interface 140 may provide one or more free form text fields where a user may type in one or more symptoms that the user may be experiencing.

With continued reference to FIG. 1, computing device 104 is configured to output self-treatment remedies as a function of generating symptomatic model 128. Self-treatment remedies may include any of the self-treatment remedies as described above. For instance and without limitation, symptomatic model 128 may receive an input containing one or more symptoms that a user may be experiencing such as stiff neck muscles upon waking and acute neck pain and output self-treatment remedies as a function of generating symptomatic model 128 that include a non-steroidal anti-inflammatory drug (NSAID) and application of a heating pad to the affected area.

With continued reference to FIG. 1, system 100 may include an image device 144. "Image device 144" as used in this disclosure, includes any device suitable to take a picture or photograph of a self-treatment remedy 108. Image device 144 may include for example, a camera, mobile phone camera, scanner or the like. Computing device 104 may be configured to receive at image device 144 any transmission from a remote device 136 containing a picture of a self-treatment remedy 108. For instance and without limitation, a user may take a photograph of a self-treatment remedy 108 using a camera located on remote device 136, such as a mobile phone camera while user is located in a pharmacy or store and seeking to purchase a self-treatment remedy 108. In yet another non-limiting example, a user may scan a photograph containing a self-treatment remedy 108 identifier such as a national drug code (NDC) while a user contemplates the purchase of one or more self-treatment remedies while in a pharmacy or grocery store for example. National drug code includes a unique 10-12 digit, 3 segment number that contains a universal product identifier for a self-treatment remedy 108.

With continued reference to FIG. 1, computing device 104 is configured to identify a self-treatment remedy 108 by retrieving an element of previous user activity data. An "element of previous user activity data" as used in this disclosure, is any self-treatment remedy 108 that a user may have previously encountered. A previous encounter may include a self-treatment remedy 108 that a user considered purchasing in a store when user experienced symptoms such as itchiness and sneezing whenever user ventured outside during the spring season. A previous encounter may include a self-treatment remedy 108 that was suggested by a family member or friend that user should consider taking because the family member or friend had utilized the self-treatment remedy 108 or knew of someone who had and had experienced a positive outcome with the particular self-treatment remedy 108. For instance and without limitation, an element of previous user activity data may include a recommendation from user's sister that suggests user try loratadine to relieve user's stuffy nose because user's sister has utilized loratadine to relieve her stuffy nose and has experienced positive results from doing so. A previous encounter may include a self-treatment remedy 108 that user tried in the past and which did not relieve user's symptoms. For instance and without limitation, a previous encounter may include a description of user's previous attempt to utilize topical clotrimazole to eliminate toe fungus and the inability of topical clotrimazole to completely eliminate user's toe fungus.

With continued reference to FIG. 1, computing device 104 is configured to classify using a remedy classifier 148 an identified self-treatment remedy as an input and output a self-treatment model. "Remedy classifier" as used in this disclosure, is a classifier implemented by a classification algorithm that maps input data to a category. A classifier includes any machine-learning model generated using a classification algorithm. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, remedy classifier 148 utilizes an identified self-treatment remedy 108 as an input and outputs a self-treatment model 152 utilizing any of the classification algorithms as described herein. A "self-treatment model" as used in this disclosure, is a machine-learning model that utilizes a biological extraction 116 as an input and outputs a remedy label. Self-treatment model 152 may include performing a series of one or more calculations, algorithms, and/or equations. Self-treatment model 152 may be generated using one or more machine-learning algorithms including any of the machine-learning algorithms as described above. Self-treatment model 152 may be generated using an unsupervised machine-learning algorithm, a supervised machine-learning algorithm, a semi-supervised machine-learning algorithm, reinforcement learning and the like.

With continued reference to FIG. 1, classifying utilizing remedy classifier 148 may include receiving an element of use allergy data. "User allergy data" as used in this disclosure, is a description of a product or ingredient that may cause a user to exhibit an allergic response when a user comes into contact with the product or ingredient. An allergic response may include a hypersensitivity of the immune system to one or more substances contained in the environment. An allergic response may include hay fever, food allergies, atopic dermatitis, allergic asthma, and/or anaphylaxis. An allergic response may trigger one or more symptoms including red eyes, itchy rash, sneezing, a runny nose, shortness of breath, and/or swelling. An allergic response may include a type 1 reaction that involves immunoglobulin E antibody (IGE) mediate release of histamine and other mediators from mast cells and basophils. This may include for example, anaphylaxis and allergic rhino conjunctivitis. An allergic response may include a type 2 reaction that may include a cytotoxic reaction that may be mediated by immunoglobulin G antibody (IGG) and/or immunoglobulin M antibody (IGM). An allergic response may include a type 3 reaction that may include an immune complex reaction that may be medicated by IGG and/or IGM antibodies. An allergic response may include a type 4 reaction that may include a cell-mediated delayed hypersensitivity reaction that may be mediated by T-cells and macrophages. An allergic response may include a food intolerance or food sensitivity that may occur when a user has difficulty digesting a particular food. A food tolerance or food sensitivity may cause one or more symptoms that include intestinal gas, abdominal pain, abdominal bloating, abdominal cramping, rashes, headache, nausea, fatigue, runny nose, reflux, flushing of skin and diarrhea. A food intolerance or sensitivity may occur in response to one or more foods such as dairy products, gluten, caffeine, salicylates, amines, FODMAPs that include fermentable; oligosaccharides; disaccharides; monosaccharides; and polyols, sulfites, fructose, aspartame, eggs, monosodium glutamate (MSG), food colorings, yeast, and sugar alcohols. A product or ingredient that may cause a user to exhibit an allergic response may include airborne allergens such as pollen, animal dander, dust mites and mold, foods such as peanuts, tree nuts, wheat, soy, fish, shellfish, eggs, and milk, insect stings such as from a bee or wasp, medications such as penicillin's, sulfa containing drug products, anticonvulsants, aspirin, ibuprofen, and chemotherapy drugs, and latex containing products. An element of user allergy data 156 may include a description of a particular ingredient or product that may cause a user to experience an allergic reaction and a description of one or more responses that the user exhibits in response to exposure to the particular ingredient or product. For example, an element of user allergy data 156 may describe a user's allergic response upon exposure to Yellow 5 dye such as tartrazine, which includes hives and swelling. In yet another non-limiting example, an element of user allergy data 156 may describe a user's allergic response upon consumption of non-steroidal anti-inflammatory drugs (NSAIDS) such as ibuprofen and naproxen which may cause urticaria, intense itching, pain, and a scratchy throat.

With continued reference to FIG. 1, computing device 104 may receive an element of user allergy data 156 from a remote device 136 operated by a user. Remote device 136 may include any of the remote device 136 as described above. In an embodiment, one or more elements of user allergy data 156 may be stored in response database. Response database may be implemented, without limitation, as a relational database, a key-value retrieval datastore such as a NOSQL database, or any other form or structure for use as a datastore that a person skilled in the art would recognize as suitable upon review of the entirety of this disclosure. Remedy classifier 148 may utilize an element of user allergy data 156 and an identified self-treatment remedy 108 as an input and output a self-treatment model 152.

With continued reference to FIG. 1, computing device 104 may receive an element of user current treatment data 160. An "element of user current treatment data" as used in this disclosure, is a list of one or more medications that a user is currently taking. Medications may include prescription medications, herbal products, vitamins, minerals, supplements, nutrients, one or more self-treatment remedies and the like. For instance and without limitation, an element of user current treatment data 160 may describe a prescription medication a user may consume such as sumatriptan for migraine prophylaxis, along with user's current vitamin regimen that includes a multivitamin, fish oil, resveratrol, and magnesium taurate. In yet another non-limiting example, an element of user current treatment data 160 may include a description of a topical prescription hydrocortisone cream user may apply at night to skin patches for eczema, along with a description of an oral steroid such as prednisone user takes sporadically when user's eczema flares up. Remedy classifier 148 utilizes an identified self-treatment remedy and an element of user current treatment data 160 as an input and outputs a self-treatment model 152.

With continued reference to FIG. 1, computing device 104 is configured to retrieve a biological extraction 116 associated with a user. A biological extraction 116 includes any of the biological extraction 116 as described above. In an embodiment, computing device 104 may retrieve a biological extraction 116 associated with a user from response database. Response database may contain one or more stored biological extraction 116 associated with a user.

With continued reference to FIG. 1, computing device 104 is configured to cocirculate a self-treatment model 152 using a machine-learning algorithm. Self-treatment model 152 includes any of the self-treatment model 152 as described above. Self-treatment model 152 utilizes a user biological extraction 116 as an input and outputs a remedy label 164. A "remedy label," as used in this disclosure, is an indication as to whether an identified self-treatment remedy 108 is appropriate to be consumed by a user and is compatible with a user's body, or whether a self-treatment remedy 108 is not appropriate to be consumed by a user and is not compatible with a user's body. For instance and without limitation, an identified self-treatment remedy 108 such as diphenhydramine may be utilized by computing device 104 in combination with self-treatment model 152 and a user biological extraction 116 to generate a remedy label 164 that indicates diphenhydramine is not appropriate to be consumed by a user and that diphenhydramine is not compatible with the user's body. In an embodiment, a remedy label 164 may indicate that a self-treatment remedy 108 may be appropriate to be consumed by a user at a certain dose, such as aspirin which may be appropriate for a user in an 81 mg dose but not in a 100 mg dose. In an embodiment, a remedy label 164 may indicate that a self-treatment remedy 108 may be appropriate to be utilized and/or consumed by a user at a certain frequency, such as benzocaine gel which may be appropriate for a user to apply to user's mouth no more than three times each week. In an embodiment, a remedy label 164 may specify a specific start and/or stop date as to when treatment with a self-treatment remedy 108 should be initiated and then stopped. For instance and without limitation, a self-treatment remedy 108 such as a shampoo to eliminate hair lice may contain a remedy label 164 that indicates a user should apply the shampoo immediately upon purchase, reapply it twice daily for a week and then stop the use of the shampoo in exactly seven days. In an embodiment, a remedy label 164 may specify at what point during treatment a user should contact a health professional if a user does not experience any improvement in symptoms. In an embodiment, a remedy label 164 may indicate one or more alternative self-treatment remedies that a user may consider using and which may be compatible with a user's body if an identified self-treatment remedy 108 is determined to not be compatible with a user's body. For instance and without limitation, an identified self-treatment remedy 108 that contains fexofenadine may be determined to be incompatible with a user's body and as such a remedy label 164 may indicate as much, and remedy label 164 may indicate one or more other self-treatment remedies that may be compatible with a user's body that may be related to the identified self-treatment remedy 108. In such an instance, remedy label 164 may indicate that one or more related self-treatment remedies such as cetirizine, levocetirizine, and loratadine may be compatible with the user's body. A self-treatment remedy 108 related to an identified self-treatment remedy 108 may include a self-treatment remedy 108 that is in the same drug class, has the same mechanism of action, has a similar chemical structure, is utilized for the same intended purpose and the like. For instance and without limitation, an identified self-treatment remedy 108 such as naproxen may be related to one or more other self-treatment remedies that are considered analgesics including acetaminophen, ibuprofen, diclofenac, and aspirin. In yet another non-limiting example, an identified self-treatment remedy 108 such as doxylamine succinate utilized as a sleep aid may be related to one or more other self-treatment remedies that are considered sleep aids such as diphenhydramine, melatonin, and valerian root.

With continued reference to FIG. 1, computing device 104 is configured to generate a remedy label 164 using a first biological extraction 116 and a self-treatment model 152. Remedy label 164 may be generated using one or more machine-learning algorithms including any of the machine-learning algorithms as described above. Computing device 104 determines using a remedy label 164 if the identified self-treatment remedy 108 associated with a user is safe for user consumption. Computing device 104 may determine that a remedy label 164 is safe to for user consumption when the remedy label 164 indicates that an identified self-treatment remedy 108 is compatible with a user's body and is appropriate to be consumed by a user. In an embodiment, indication as to whether an identified self-treatment remedy is compatible with a user's body may be stored in a database such as in response database. In such an instance, computing device 104 may retrieve from a database an indication as to whether an identified self-treatment remedy is compatible with a user's body. Computing device 104 may determine that a remedy label 164 is not safe to be consumed by a user when the remedy label 164 indicates that an identified self-treatment remedy 108 is not compatible with a user's body and is not appropriate to be consumed by a user. An identified self-treatment remedy 108 that is considered to be safe for a user may include a self-treatment remedy 108 that will not cause unnecessary adverse effects, is considered safe and effective to be consumed or used by the user and will not cause intentional harm to the user's body. An identified self-treatment remedy 108 that is considered to not be safe for a user may include a self-treatment remedy 108 that will cause unnecessary adverse effects, is not considered safe and effective to be consumed or used by the user and may cause intentional harm to the user's body. For instance and without limitation, an identified self-treatment remedy 108 such as BENADRYL as produced by Johnson & Johnson of New Brunswick, New Jersey may be considered not safe for a user with a known anaphylactic allergy to red 40, because BENADRYL as produced by Johnson & Johnson of New Brunswick, New Jersey contains red 40 and administration would cause harm and unnecessary adverse effects. In yet another non-limiting example, an identified self-treatment remedy 108 that is considered to not be safe for a user may include a self-treatment remedy 108 such as ibuprofen for a user with a known genetic marker containing a mutated SLCO1B1 gene as consumption of ibuprofen and other non-steroidal anti-inflammatory drugs (NSAIDS) by users with a known mutated SLCO1B1 gene may triple a user's risk for experiencing a myocardial infarction (MI).

With continued reference to FIG. 1, determining using the remedy label 164 if the identified self-treatment remedy 108 is safe for user consumption may include retrieving an element of user metabolic data 168. "Metabolic data 168" as used in this disclosure, includes a marker of metabolism. Metabolic data 168 may include data relating to absorption, distribution, metabolism, and elimination of self-treatment remedies. Absorption may include the ability of a self-treatment remedy 108 to reach a tissue such as via mucous surfaces such as intestinal absorption in the digestive tract. Absorption may be altered by factors such as an alerted microbiome. For example, a user who has leaky gut syndrome may not adequately absorb an analgesic such as ibuprofen or acetaminophen and instead may require a topical analgesic such as topical diclofenac cream. Absorption may also be altered by other factors such as gastric emptying time which can be affected by medical conditions such as diabetes that can cause gastroparesis and delayed gastrointestinal emptying time. Absorption may be altered by chemical instability of a self-treatment remedy 108 in the stomach, and the inability of a self-treatment remedy 108 to permeate the intestinal wall thereby reducing the extent to which a self-treatment remedy 108 is absorbed. Absorption may also affect bioavailability of a self-treatment remedy 108 as self-treatment remedy 108 that are poorly absorbed may have very little bioavailability and as such may need to be administered in an alternative dosage form. Distribution may include the ability of a self-treatment remedy 108 to be carried to its effector site, such as through the bloodstream. After passage through the bloodstream, a self-treatment remedy 108 may be distributed to one or more muscles and organs. The ability of a self-treatment remedy 108 to be distributed to one or more locations in the body may be affected by factors such as regional blood flow rates, molecular size, polarity and binding to serum proteins, and forming a complex. For example, a self-treatment remedy 108 such as levocarnitine is unable to be distributed across the blood brain barrier and as such acts systemically in the body outside of the blood brain barrier, while acetyl-1-carnitine is able to be distributed across the blood brain barrier and is effectively utilized for neurological conditions including memory issues and tremors seen in individuals with Parkinson's disease. Metabolism includes the ability of a self-treatment remedy 108 to be broken down as it enters the body. Metabolism may be carried out by the liver through redox enzymes or cytochrome P450 enzymes. As a self-treatment remedy 108 is metabolized, it may be converted to one or more new compounds known as metabolites. Excretion includes the ability of a self-treatment remedy 108 and its metabolites to be removed from the body via excretion such as through the kidneys and eventually into urine and/or in the feces. Excretion can occur at the kidneys where a self-treatment remedy 108 is excreted into urine. Excretion can occur in biliary tract where excretion begins in the liver and passes through to the gut until the self-treatment remedy 108 is excreted in urine or fecal elimination. Excretion can occur through the lungs such as by exhaling a self-treatment remedy 108.

With continued reference to FIG. 1, metabolic data may include one or more genetic markers that may alter the metabolism of a self-treatment remedy 108. "Genetic markers" as used herein, includes deoxyribonucleic acid (DNA) samples and/or sequences, such as without limitation DNA sequences contained in one or more chromosomes in human cells. Genetic markers may include, without limitation, ribonucleic acid (RNA) samples and/or sequences, such as samples and/or sequences of messenger RNA (mRNA) or the like taken from human cells. Genetic markers may include telomere lengths. Genetic markers may include epigenetic markers including data describing one or more states of methylation of genetic material. Genetic markers may include one or more polymorphisms of P450 cytochromes. For instance and without limitation, a polymorphism of CYP2C9 gene may cause altered ibuprofen metabolism, whereby a standard 400 mg dose of ibuprofen given to a user with a polymorphism of CYP2C9 gene may cause toxicity due to altered metabolism and higher concentrations penetrating the blood stream.

With continued reference to FIG. 1, computing device 104 generates a metabolic model 172. A "metabolic model 172" as used in this disclosure, includes a machine-learning model that utilizes metabolic data as an input and outputs safe treatment remedies. Safe treatment remedies include any of the safe treatment remedies as described above. Computing device 104 compares the output safe treatment remedies to the identified self-treatment remedy 108. In an embodiment, an identified self-treatment remedy 108 that matches an output safe treatment remedy may be utilized by computing device 104 to generate a remedy label 164 that indicates that the identified self-treatment remedy 108 is safe for user consumption. In an embodiment, an identified self-treatment remedy 108 that does not match an output safe treatment remedy may be utilized by computing device 104 to generate a remedy label 164 that indicates that the identified self-treatment remedy 108 is not safe for user consumption.

With continued reference to FIG. 1, computing device 104 is configured to combine bins in different ways so that an input and/or output from any machine-learning algorithm and/or machine-learning model can be combined and fed into one another. For instance and without limitation, computing device 104 may utilize an output generated from metabolic model as an input into remedy classifier. In yet another non-limiting example, an output from generating treatment model relating biological extractions to self-treatment remedies may be utilized as an input into remedy classifier. In an embodiment, remedy classifier is configured to select one or more machine-learning algorithms and/or machine-learning models to be calculated and/or generated. For instance and without limitation, remedy classifier may select an element of user allergy data to generate a supervised machine-learning algorithm. In yet another non-limiting example, remedy classifier may select an output of metabolic model to be utilized as an input into remedy classifier.

Figure 2:
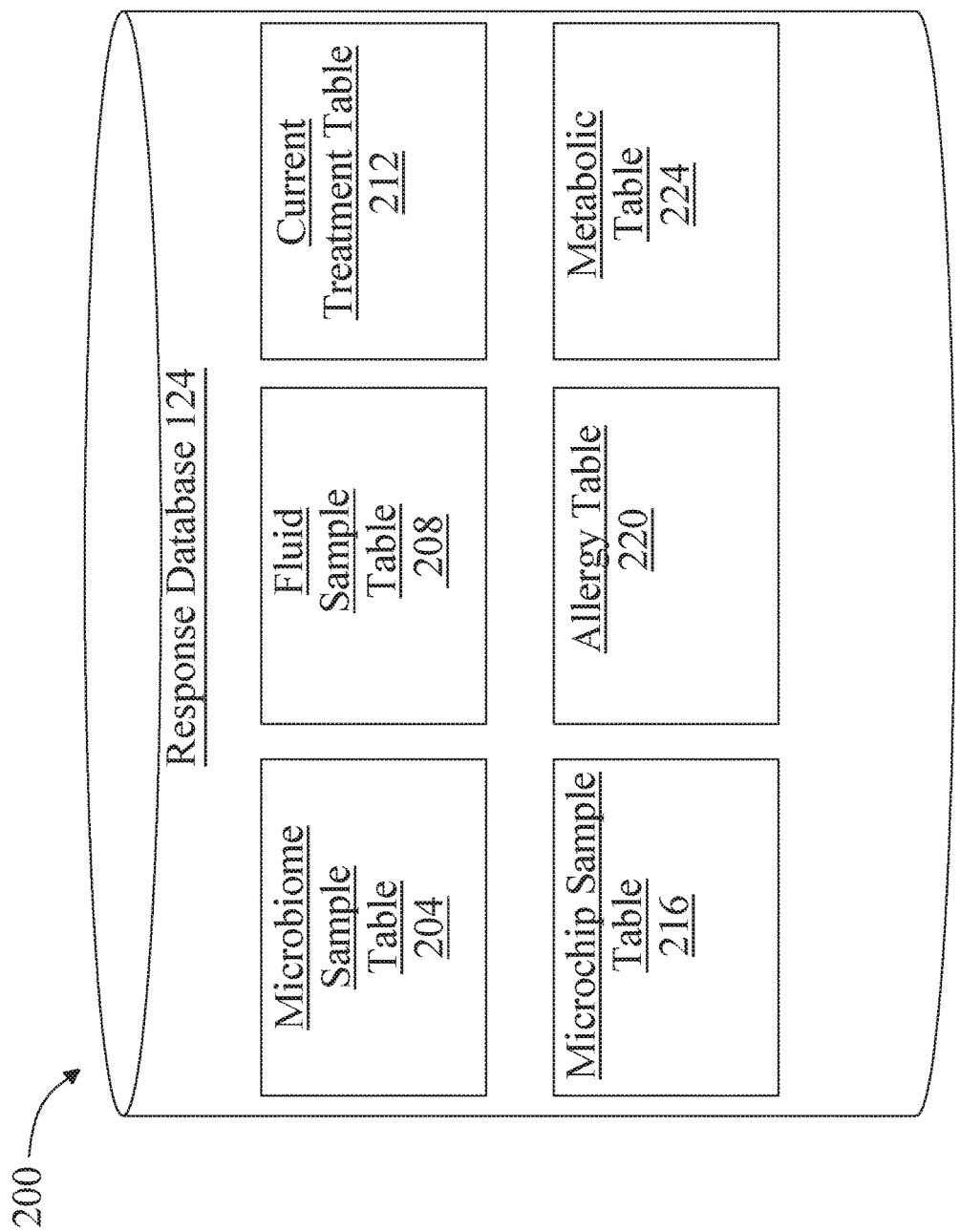
FIG. 2 is a block diagram illustrating an exemplary embodiment of a response database.

Referring now to FIG. 2, an exemplary embodiment of response database is illustrated. Response database may be implemented as any data structure as described above in more detail in reference to FIG. 1. One or more tables contained within response database may include microbiome sample table 204; microbiome sample table 204 may include one or more biological extraction 116 relating to the microbiome. For instance and without limitation, microbiome sample table 204 may include a physically extracted sample such as a stool sample analyzed for the presence of pathogenic species such as parasites and anaerobes. One or more tables contained within response database may include fluid sample table 208; fluid sample table 208 may include one or more biological extraction 116 containing fluid samples. For instance and without limitation, fluid sample table 208 may include a urine sample analyzed for the presence or absence of glucose, ketones, bacteria, nitrites, epithelial cells, white blood cells, leukocyte esterase, and ph. One or more tables contained within response database may include current treatment table 212; current treatment table 212 includes one or more current treatments that the user is currently taking, dose user is taking, frequency that user takes the treatment, how long the user has been taking the treatment and the like. For instance and without limitation, current treatment table 212 may include user's current prescriptive therapies which include lisinopril 20 mg taken once daily for the past six years and levothyroxine 50 mcg taken once daily on an empty stomach which using has been taking for the past three months, and in addition user's vitamin regimen which includes liposomal vitamin C 100 mg taken twice daily. One or more tables contained within response database may include microchip sample table 216; microchip sample table 216 may include one or more biological extraction 116 obtained from a microchip. For instance and without limitation, microchip sample table 216 may include a heart rate, blood pressure, pulse rate, and temperature reading obtained from a microchip embedded under a user's skin. One or more tables contained within response database may include allergy table 220; allergy table 220 may include a description of one or more user allergies. For instance and without limitation, allergy table 220 may include a description of user's anaphylactic reaction to shellfish and a description of hives that user experiences on user's upper torso after consuming sulfa-containing drug products. One or more tables contained within response database may include metabolic table 224; metabolic table 224 may include one or more elements of user metabolic data 168. For instance and without limitation, metabolic table 224 may include a genetic single nucleotide polymorphism (SNP) that causes user to be a poor metabolizer of acetaminophen containing drug products.

Figure 3:
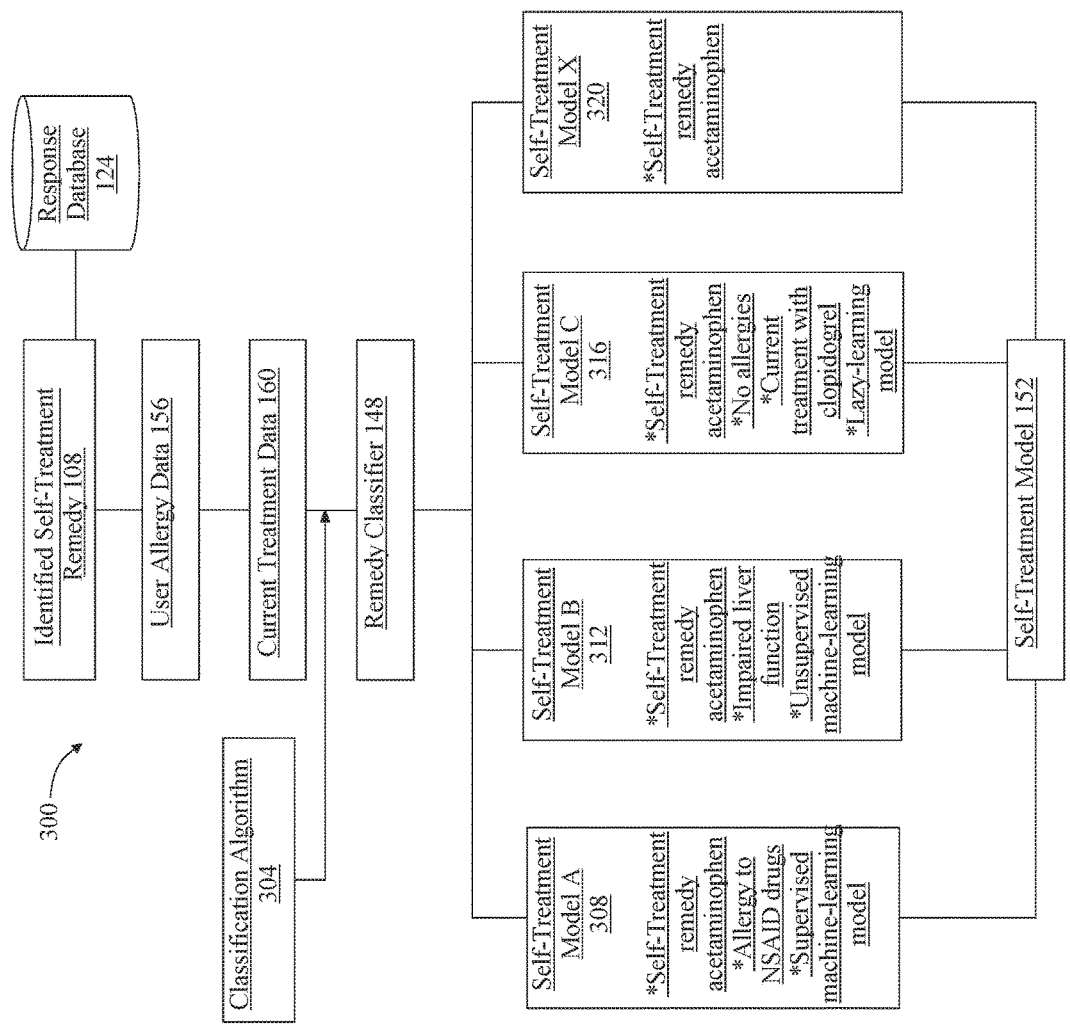
FIG. 3 is a diagrammatic representation of remedy classifier.

Referring now to FIG. 3, an exemplary embodiment of remedy classifier 148 is illustrated. Remedy classifier 148 may be generated utilizing any of the classification algorithms 304 as described above. Classification algorithms 304 may include logistic regression and/or naive Bayes classifiers, nearest neighbor classifiers including without limitation k-nearest neighbors classifiers, support vector machines, decision trees, boosted trees, random forest classifiers, and/or neural network-based classifiers. Remedy classifier utilizes an identified self-treatment remedy 108 as an input and outputs a self-treatment model 152. Identified self-treatment remedy 108 includes any of the identified self-treatment remedies as described above. For instance and without limitation, identified self-treatment remedy 108 may include diphenhydramine 25 mg tablets or identified self-treatment remedy 108 may include calcium carbonate 500 mg chewable tablets. Remedy classifier 148 may utilize one or more additional inputs in addition to an identified self-treatment remedy 108. Remedy classifier 148 may utilize an element of user allergy data 156 as an input that may be utilized by remedy classifier 148 in addition to identified self-treatment remedy 108 to select a self-treatment model 152. User allergy may include any of the user allergies as described above. For instance and without limitation, user allergy may include a user's allergy to one or more medications such as penicillin. In an embodiment, user allergy may include a user's allergy to one or more foods such as tree nuts. Remedy classifier 148 may utilize an element of current treatment data 160 as an input that may be utilized by remedy classifier 148 in addition to identified self-treatment remedy 108 to select a self-treatment model 152. Current treatment data 160 may include any of the current treatment data 160 as described above. For instance and without limitation, current treatment data 160 may include one or more prescription medications that the user may be currently taking such as losartan for high blood pressure. Current treatment data 160 may include one or more non-prescription medications that the user may be currently taking such as loratadine for allergies and calcium carbonate for heart burn.

With continued reference to FIG. 3, remedy classifier 148 generates an output containing a self-treatment model 152. In an embodiment, remedy classifier 148 generates an output containing a self-treatment model 152 for a particular identified self-treatment remedy 108. For instance and without limitation, computing device 104 may contain an infinite number of self-treatment model 152 for a first identified self-treatment remedy 108 such as acetaminophen, an infinite number of self-treatment models for a second identified self-treatment remedy 108 such as ibuprofen, an infinite number of self-treatment model 152 for a third identified self-treatment remedy 108 such as topical hydrocortisone cream and the like. In an embodiment, self-treatment model 152 may be implemented as various machine-learning models including supervised machine-learning models, unsupervised machine-learning models, lazy-learning models, support vector machines models, linear regression models, logistic regression models, naïve Bayes models, linear discriminant analysis models, decision trees, k-nearest neighbor algorithm, neural networks and the like. In an embodiment, remedy classifier 148 may select self-treatment model 152 A 308 for an identified self-treatment remedy 108 such as acetaminophen for a user who has an allergy to non-steroid anti-inflammatory drugs (NSAIDS). In an embodiment, self-treatment model 152 A may be implemented as a supervised machine-learning model. In an embodiment, remedy classifier 148 may select self-treatment model 152 B 312 for an identified self-treatment remedy 108 such as acetaminophen for a user who has impaired liver function. In an embodiment, self-treatment model 152 B may be implemented as an unsupervised machine-learning model. In an embodiment, remedy classifier 148 may select self-treatment model 152 C 316 for an identified self-treatment remedy 108 such as acetaminophen for a user who does not have any known allergies and who is currently taking the medication clopidogrel for anticoagulation purposes. In an embodiment, self-treatment model 152 C may be implemented as a lazy-learning model.

Figure 4:
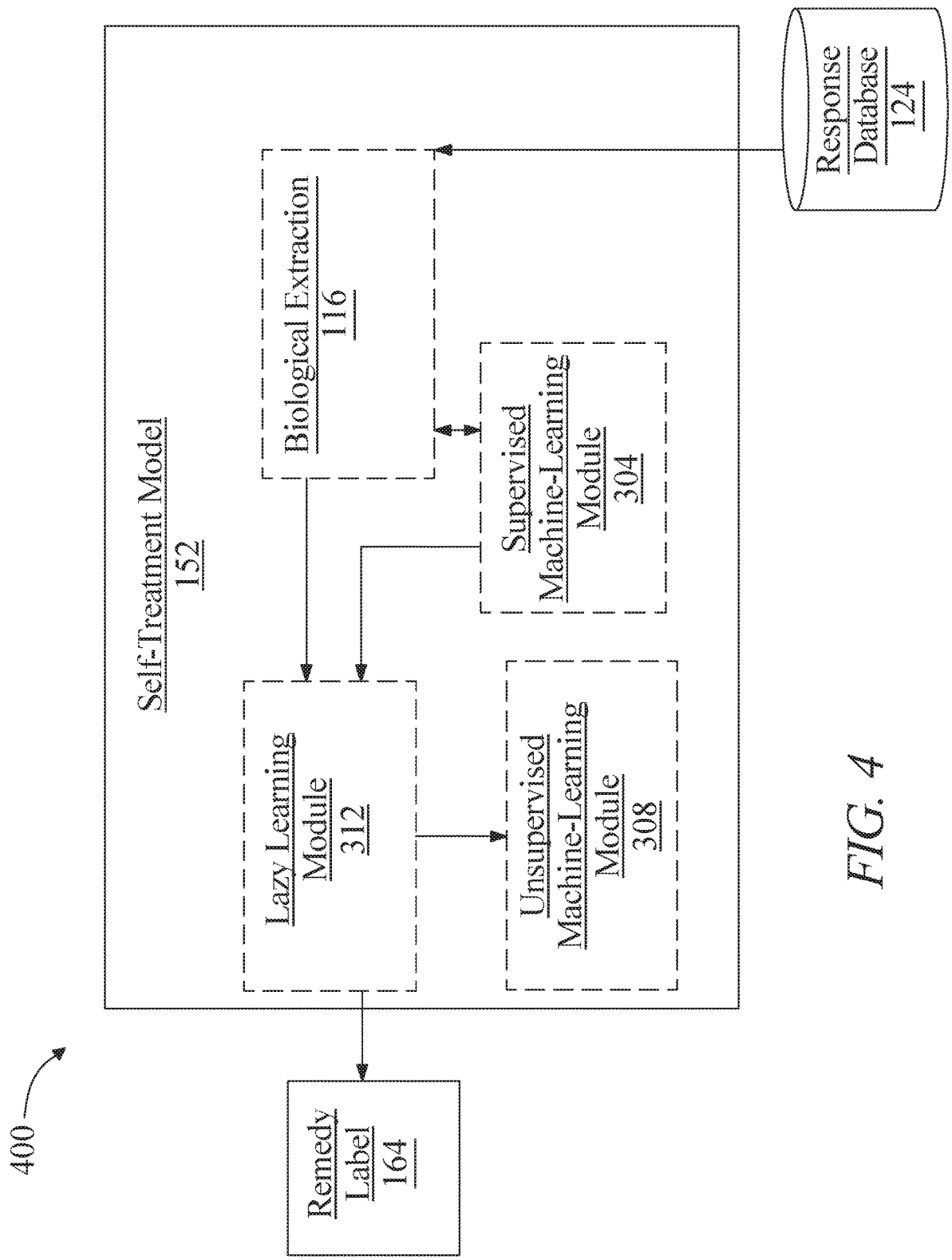
FIG. 4 is diagrammatic representation of self-treatment model.

Referring now to FIG. 4, an exemplary embodiment of self-treatment model 152 is illustrated. Self-treatment model 152 may include one or more modules that may designed and configured to calculate one or more machine-learning algorithms. Modules may be implemented as any hardware and/or software module. Self-treatment model 152 may include supervised machine-learning module 304. Supervised machine-learning algorithms, may include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning algorithm may use elements of biological extraction 116 as inputs, remedy label 164 as outputs, and a scoring function representing a desired form of relationship to be detected between elements of biological extraction 116 and remedy label 164; scoring function may, for instance, seek to maximize the probability that a given element of biological extraction 116 data and/or combination of elements of biological extraction 116 data is not associated with a given remedy label 164 and/or combination of remedy label 164. Scoring function may be expressed as a risk function representing an "expected loss" of an algorithm relating inputs to outputs, where loss is computed as an error function representing a degree to which a prediction generated by the relation is incorrect when compared to a given input-output pair provided in a training set. Self-treatment model may include unsupervised machine-learning module 308. For instance and without limitation, unsupervised machine-learning algorithms may include clustering data to detect correlations between biological extraction 116 and remedy label 164; such processes may be combined with one or more supervised machine-learning algorithms.

With continued reference to FIG. 4, self-treatment model 152 may include lazy-learning module 312. In an embodiment, one or more machine-learning algorithms including supervised machine-learning algorithms, unsupervised machine-learning algorithms and/or lazy learning algorithms may be subject to one or more domain limitations. A lazy-learning process and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover a "first guess" at a remedy label 164 associated with a biological extraction 116. As a non-limiting example, an initial heuristic may include a ranking of remedy label 164 according to relation to a test type of a biological extraction 116, and/or one or more categories of biological extractions identified. Ranking may include, without limitation, ranking according to significance scores of associations between elements of biological extraction 116 and remedy label 164. Heuristic may include selecting some number of highest-ranking associations between biological extraction 116 and remedy label 164. Lazy-learning module 312 may additionally or alternatively implement any suitable "lazy learning" algorithm, including without limitation a K-nearest neighbors algorithm, a lazy naïve Bayes algorithm, or the like.

Figure 5:
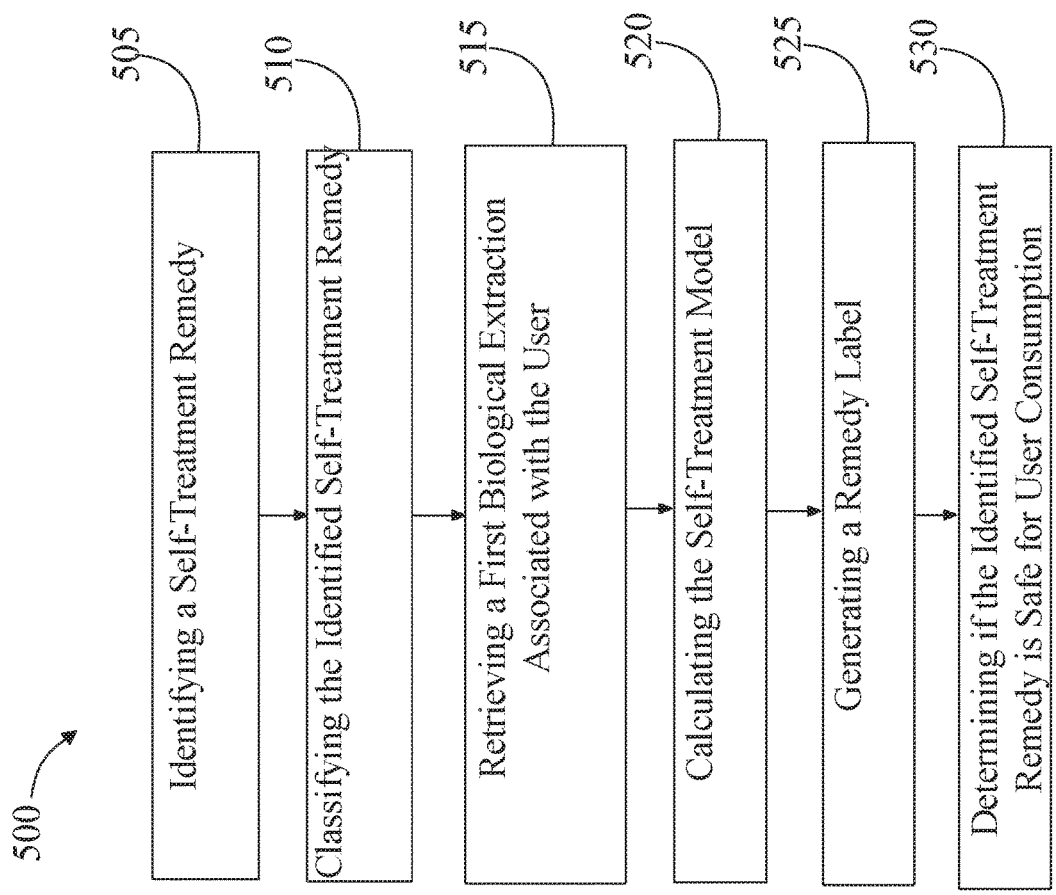
FIG. 5 is a process flow diagram illustrating an exemplary embodiment of a method of informing self-treatment remedy selection.

Referring now to FIG. 5, an exemplary embodiment 500 of a method of informing self-treatment remedy 108 selection is illustrated. At step 505 a computing device 104 identifies a self-treatment remedy 108 associated with a user. Self-treatment remedy 108 includes any of the self-treatment remedies as described above. Computing device 104 identifies a self-treatment remedy 108 by receiving treatment training data 112. Treatment training data 112 includes any of the treatment training data 112 as described above. Treatment training data 112 includes a plurality of biological extraction 116 and a plurality of correlated self-treatment remedies. Biological extraction 116 include any of the biological extraction 116 as described above in reference to FIGS. 1-4. For instance and without limitation, a biological extraction 116 may include one or more nutrient levels obtained from a sensor implanted on a user's tooth. In yet another non-limiting example, a biological extraction 116 may include a stool sample analyzed for one or more strains of bacteria and fungus such as *Salmonella, Yersinia enterocolitica, Clostridium difficile*, and the like. In yet another non-limiting example, a biological extraction 116 may include one or more vital signs obtained from a microchip implanted under a user's skin. Computing device 104 records a user biological extraction 116. Computing device 104 may record a user biological extraction 116 in response database. Computing device 104 generates using a machine-learning algorithm a treatment model 120 relating biological extraction 116 to self-treatment remedies. Machine-learning algorithm includes any of the machine-learning algorithms as described above in reference to FIGS. 1-4. Treatment model 120 includes any of the treatment model 120 as described above in reference to FIGS. 1-4. Treatment model 120 outputs one or more self-treatment remedies. For instance and without limitation, treatment model 120 may output a self-treatment remedy 108 such as lidocaine 5% topical cream. In yet another non-limiting example, treatment model 120 may output a self-treatment remedy 108 such as permethrin cream rinse.

With continued reference to FIG. 5, identifying self-treatment remedy 108 includes receiving symptomatic training data 124 by computing device 104. Symptomatic training data 124 includes a plurality of symptoms and a plurality of correlated self-treatment remedies. Symptoms include any of the symptoms as described above in reference to FIGS. 1-4. Computing device 104 receives a user symptom 132. In an embodiment, user symptom 132 may be received from remote device 136. In an embodiment, user symptom 132 may be entered by a user at graphical user interface 140 located on computing device 104. User symptom 132 may include a description of one or more symptoms the user may be experiencing. For instance and without limitation, user symptom 132 may include a description of sharp throbbing back pain user is experiencing for the past three days. In yet another non-limiting example, user symptom 132 may include a description of intense itching, and a tickling feeling that a user experiences from movement on user's head and scalp. Computing device 104 generates using a machine-learning algorithm a symptomatic model 128 relating symptoms to self-treatment remedies. Machine-learning algorithm may include any of the machine-learning algorithms as described above, including for example a supervised machine-learning algorithm or an unsupervised machine-learning algorithm. Computing device 104 outputs self-treatment remedies as a function of generating symptomatic model 128. For instance and without limitation, computing device 104 may receive a user symptom 132 that includes a complaint of cough, sore throat, and headache, and utilize symptomatic model 128 to output a self-treatment remedy 108 that includes guaifenesin.

With continued reference to FIG. 5, computing device 104 may identify a self-treatment remedy 108 by receiving at an image device 144 located on computing device 104 a wireless transmission from remote device 136 containing a picture of a self-treatment remedy 108. For instance and without limitation, a user may find a self-treatment remedy 108 at home in user's medicine cabinet and take a picture the self-treatment remedy 108 using an image device 144 located on remote device 136 such as a cell phone camera. In such an instance, computing device 104 may receive a wireless transmission from remote device 136 containing a picture of the self-treatment remedy 108 that user located in user's medicine cabinet. In yet another non-limiting example, a user may experience symptoms such as sneezing, runny nose, and a dry cough during peak spring allergy system and travel to a pharmacy to locate a self-treatment remedy 108 to alleviate user's symptoms. In such an instance, user may take a picture of a self-treatment remedy 108 user locates in the pharmacy with image device 144 located in user's remote device 136 such as a cell phone or tablet. Computing device 104 may identify a self-treatment remedy 108 by retrieving an element of previous user activity data. In an embodiment, an element of previous user activity data may be stored in response database. Previous user activity data may include a previously utilized self-treatment remedy 108 by a user. A previously utilized self-treatment remedy 108 may include any self-treatment remedy 108 that a user had a previous encounter with. For instance and without limitation, a previously utilized self-treatment remedy may include a self-treatment remedy 108 that user took in the past when user experienced the same or similar symptoms. For example, a previously utilized self-treatment remedy 108 may include topical A and D ointment that a user applied to user's itchy feet three months prior.

With continued reference to FIG. 5, at step 510 a computing device classifies using a remedy classifier 148 an identified self-treatment remedy 108 as an input and outputs a self-treatment model 152. Remedy classifier 148 may be generated utilizing any of the classification algorithms as described above in reference to FIGS. 1-4. For instance and without limitation, classification algorithms may include one or more logistic regression algorithms, k-nearest neighbor algorithm, support vector machine, decision tree, boosted tree, random forest, and/or neural networks. Classifying utilizing remedy classifier 148 may include utilizing additional inputs in conjunction with an identified self-treatment remedy 108. Computing device 104 may receive an element of user allergy data 156. User allergy data 156 may include any of the user allergy data 156 as described above in reference to FIGS. 1-4. For example, user allergy data 156 may include any known drug allergies such as an allergy to aminoglycosides. User allergy data 156 may include a known food allergy such as a user's food intolerance to onion and garlic. User allergy may include a known chemical allergy such as a user's allergy to yellow food dye #5 and brilliant blue #2. Remedy classifier 148 utilizes an identified self-treatment remedy 108 and an element of user allergy data 156 as an input and outputs a self-treatment model 152. Computing device 104 may receive an element of user current treatment data 160. User current treatment data 160 includes any of the current treatment data 160 as described above in reference to FIGS. 1-4. In an embodiment, user current treatment data 160 may include one or more prescription medications that a user may be currently taking such as doxycycline for acne. User current treatment data 160 may include one or more non-prescription medications the user may be currently taking such as a vitamin, supplement, or other self-treatment remedies. For example, user current treatment data 160 may include cetirizine that the user takes on a daily basis to help alleviate user's allergies. Computing device 104 classifies using an identified self-treatment remedy 108 and an element of user current treatment data 160 as an input and outputs a self-treatment model 152. Self-treatment model 152 includes any of the self-treatment model 152 as described above in reference to FIGS. 1-4.

With continued reference to FIG. 5, at step 515 computing device 104 retrieves a first biological extraction 116 associated with a user. First biological extraction 116 may include without limitation any biological extraction suitable for use as a biological extraction as described above in reference to FIGS. 1-4. One or more biological extraction 116 may be stored in response database.

With continued reference to FIG. 5, at step 520 computing device 104 calculates using a self-treatment model 152 using a first machine-learning algorithm, wherein the self-treatment model 152 takes a user biological extraction 116 as an input and outputs a remedy label 164. First machine-learning algorithm may include without limitation any machine-learning algorithm or combination of machine-learning algorithms as described above in reference to FIGS. 1-4. First machine-learning algorithm may include, as a non-limiting example, a supervised machine-learning algorithm, or an unsupervised machine-learning algorithm. Remedy label 164 includes an indication as to whether an identified self-treatment remedy 108 is appropriate to be consumed by a user and is compatible with a user's body, or whether a self-treatment remedy 108 is not appropriate to be consumed by a user and is not compatible with a user's body. In an embodiment, remedy label 164 may list one or more self-treatment remedies that may be compatible with a user's body if an identified self-treatment remedy 108 is not compatible with a user's body. Remedy label 164 may include a proposed dose of an identified self-treatment remedy 108 that may be compatible with a user's body. For instance and without limitation, a remedy label 164 may indicate that diphenhydramine is compatible with a user's body at a dose of 25 mg and below but any dose of 25 mg and higher is not compatible with a user's body.

With continued reference to FIG. 5, at step 525 computing device 104 generates a remedy label 164 utilizing a first biological extraction 116 and a self-treatment model 152. Computing device 104 generates a remedy label 164 utilizing any of the methods as described above in reference to FIGS. 1-4.

With continued reference to FIG. 5, at step 530 computing device 104 determines using a remedy label 164 if an identified self-treatment remedy 108 is safe for user consumption. Computing device 104 may determine that an identified self-treatment remedy 108 is safe for user consumption if a remedy label 164 indicates that it is appropriate to be consumed by a user and is compatible with a user's body. Computing device 104 may determine that an identified self-treatment remedy 108 is not safe for user consumption if a remedy label 164 indicates that it is not appropriate to be consumed by a user and is not compatible with a user's body. Computing device 104 may determine that an identified self-treatment remedy 108 is safe for user consumption by utilizing user metabolic data 168. Computing device 104 may retrieve an element of user metabolic data 168. In an embodiment, user metabolic data 168 may be contained within response database. User metabolic data 168 includes any of the user metabolic data 168 as described above in reference to FIG. 1. For instance and without limitation, user metabolic data 168 may indicate a user's genetic polymorphism that results in a user producing less UDP-glucuronosyl transferase (UGT) and thus having increased systemic levels of acetaminophen and therefore being more susceptible to acetaminophen toxicity. In yet another non-limiting example, user metabolic data 168 may indicate a user's altered gut wall lining that causes the user to have altered metabolism of orally administered medications. Computing device 104 generates a metabolic model 172 wherein the metabolic model 172 utilizes an element of user metabolic data 168 as an input and outputs safe treatment remedies. Metabolic model 172 includes any of the metabolic model 172 as described above in reference to FIGS. 1-4. Safe treatment remedies include any of the safe treatment remedies as described above. Safe treatment remedies may include self-treatment remedies that are considered compatible with a user's body. Computing device 104 compares output safe treatment remedies to an identified self-treatment remedy 108. Computing device 104 may determine that an identified self-treatment remedy 108 is safe for user consumption if an identified self-treatment remedy 108 matches an output safe treatment remedy. Computing device 104 may determine that an identified self-treatment remedy 108 is not safe for user consumption if an identified self-treatment remedy 108 does not match an output safe treatment remedy.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
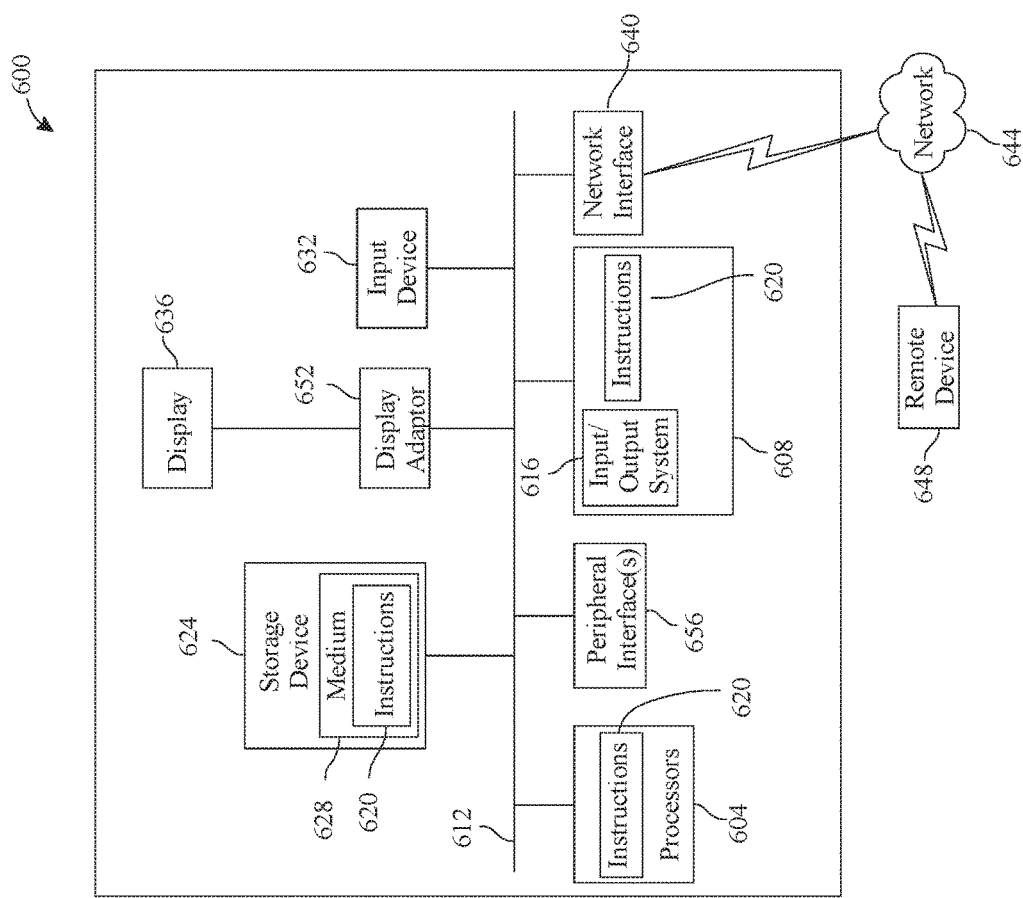
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Memory 608 may include various components (e.g., machine-readable media) including, but not limited to, a random access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIRE-WIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote device 136 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for informing self-treatment remedy selection, the system comprising a computing device, the computing device designed and configured to:
   identify a self-treatment remedy associated with a user, wherein identifying the self-treatment remedy associated with the user comprises:
      generating a machine-learning treatment model, wherein generating the machine-learning treatment model comprises:
         training the machine-learning treatment model using a first machine learning algorithm and treatment training data, wherein the treatment training data comprises a plurality of biological extractions comprising at least a user body measurement including an epigenetic body measurement of a user disease state describing changes to a user genome that do not involve corresponding changes in a user nucleotide sequence, and a plurality of correlated self-treatment remedies;
         receiving a first user biological extraction; and
         outputting, using the trained machine-learning treatment model, a first potential self-treatment remedy, wherein the first user biological extraction is provided to the trained machine-learning treatment model as an input to output the first potential self-treatment remedy;
      generating a machine-learning symptomatic model, wherein generating the machine-learning symptomatic model comprises:
         training the machine-learning symptomatic model using a second machine learning algorithm and symptomatic training data, wherein the symptomatic training data comprises a plurality of symptoms and a plurality of correlated self-treatment remedies;
         receiving a user symptom; and
         outputting, using the trained machine-learning symptomatic model, a second potential self-treatment remedy, wherein the first user biological extraction is provided to the trained machine-learning symptomatic model as an input to output the second potential self-treatment remedy;
      determining an identifier from a scan received from a user device associated with the user; and
      generating the identified self-treatment remedy as a function of the first potential self-treatment remedy, the second potential self-treatment remedy and the identifier;
   classify, using a remedy classifier, the identified self-treatment remedy;
   generate, using the remedy classifier, a self-treatment model based upon the classification of the identified self-treatment remedy, said self-treatment model comprising a third machine learning algorithm configured to receive a second user biological extraction as an input and output a remedy label, wherein generating the self-treatment model comprises training the self-treatment model according to the classification of the identified self-treatment remedy, wherein said remedy label indicates whether the identified self-treatment remedy is safe for consumption by the user;
   determine, using the remedy label, an indication of safety for user consumption of the identified self-treatment remedy, wherein determining the indication of safety comprises:
      retrieving an element of user metabolic data relating to absorption, distribution, metabolism, and elimination of self-treatment remedies;
   generate a metabolic model, wherein the metabolic model comprises a trained machine-learning model configured to receive the element of user metabolic data associated with the user as an input and output at least one safe treatment remedy based on the absorption, distribution, metabolism, and elimination of self-treatment remedies; and
   compare the at least one safe treatment remedy to the identified self-treatment remedy.

2. The system of claim 1, wherein identifying the self-treatment remedy further comprises receiving at an image device located on the computing device a wireless transmission from a remote device containing a picture of the self-treatment remedy.

3. The system of claim 1, wherein identifying the self-treatment remedy further comprises retrieving an element of previous user activity data comprising a previously utilized self-treatment remedy.

4. The system of claim 1, wherein generating the self-treatment model further comprises:
   classifying an element of user allergy data; and
   generating, using the remedy classifier, the self-treatment model further based upon the classification of the element of user allergy data.

5. The system of claim 1, wherein generating the self-treatment model further comprises:
   classifying an element of user current treatment data; and
   generating, using the remedy classifier, the self-treatment model further based upon the classification of the element of user current treatment data.

6. The system of claim 1, wherein the self-treatment model further comprises a supervised machine-learning algorithm.

7. The system of claim 1, wherein the self-treatment model further comprises an unsupervised machine-learning algorithm.

8. The system of claim 1, wherein the user metabolic data includes remedy absorption data.

9. The system of claim 1, wherein the safe treatment remedy includes an over the counter medication.

10. A method of informing self-treatment remedy selection, the method comprising:
    identifying, by a computing device, a self-treatment remedy associated with a user, wherein identifying the self-treatment remedy associated with the user comprises:
       generating a machine-learning treatment model, wherein generating the machine-learning treatment model comprises:
          training the machine-learning treatment model using a first machine learning algorithm and treatment training data, wherein the treatment training data comprises a plurality of biological extractions comprising at least a user body measurement including an epigenetic body measurement of a user disease state describing changes to a user genome that do not involve corresponding changes in a user nucleotide sequence, and a plurality of correlated self-treatment remedies;

receiving a first user biological extraction; and outputting, using the trained machine-learning treatment model, a first potential self-treatment remedy, wherein the first user biological extraction is provided to the trained machine-learning treatment model as an input to output the first potential self-treatment remedy;

generating a machine-learning symptomatic model, wherein generating the machine-learning symptomatic model comprises:

training the machine-learning symptomatic model using a second machine learning algorithm and symptomatic training data, wherein the symptomatic training data comprises a plurality of symptoms and a plurality of correlated self-treatment remedies;

receiving a user symptom; and outputting, using the trained machine-learning symptomatic model, a second potential self-treatment remedy, wherein the first user biological extraction is provided to the trained machine-learning symptomatic model as an input to output the second potential self-treatment remedy;

determining an identifier from a scan received from a user device associated with the user; and generating the identified self-treatment remedy as a function of the first potential self-treatment remedy, the second potential self-treatment remedy and the identifier;

classifying, by the computing device using a remedy classifier, the identified self-treatment remedy;

generating, by the computing device using the remedy classifier, a self-treatment model based upon the classification of the identified self-treatment remedy, said self-treatment model comprising a third machine learning algorithm configured to receive a second user biological extraction as an input and output a remedy label, wherein generating the self-treatment model comprises training the self-treatment model according to the classification of the identified self-treatment remedy, wherein said remedy label indicates whether the identified self-treatment remedy is safe for consumption by the user;

determining, using the remedy label, an indication of safety for user consumption of the identified self-treatment remedy, wherein determining the indication of safety comprises:

retrieving an element of user metabolic data relating to absorption, distribution, metabolism, and elimination of self-treatment remedies;

generating a metabolic model, wherein the metabolic model comprises a trained machine-learning model configured to receive the element of user metabolic data as an input and output at least one safe treatment remedy based on the absorption, distribution, metabolism, and elimination of self-treatment remedies; and comparing the at least one safe treatment remedy to the identified self-treatment remedy.

11. The method of claim 10, wherein identifying the self-treatment remedy further comprises receiving at an image device located on the computing device a wireless transmission from a remote device containing a picture of the self-treatment remedy.

12. The method of claim 10, wherein identifying the self-treatment remedy further comprises retrieving an element of previous user activity data comprising a previously utilized self-treatment remedy.

13. The method of claim 10, wherein generating the self-treatment model further comprises:

classifying an element of user allergy data; and generating, using the remedy classifier, the self-treatment model further based upon the classification of the element of user allergy data.

14. The method of claim 10, wherein generating the self-treatment model further comprises:

classifying an element of user current treatment data;

generating, using the remedy classifier, the self-treatment model further based upon the classification of the element of user current treatment data.

15. The method of claim 10, wherein the self-treatment model further comprises a supervised machine-learning algorithm.

16. The method of claim 10, wherein the self-treatment model further comprises an unsupervised machine-learning algorithm.

17. The method of claim 10, wherein the user metabolic data includes remedy absorption data.

18. The method of claim 10, wherein the safe treatment remedy includes an over the counter medication.

* * * * *